(12) United States Patent
Rager

(10) Patent No.: US 11,684,600 B2
(45) Date of Patent: Jun. 27, 2023

(54) COMPOSITION OF ACTIVE AGENTS TO POSITIVELY AFFECT A ROBUST MAMMALIAN ENDOCANNABINOID SYSTEM TONE TO BETTER ADDRESS AGE RELATED DISCOMFORT

(71) Applicant: Compact Disc Incorporated, Silver Spring, MD (US)

(72) Inventor: Robert Rager, Silver Spring, MD (US)

(73) Assignee: COMPACT DISC INCORPORATED, Silver Spring, MD (US)

( * ) Notice: Subject to any disclaimer, the term of this patent is extended or adjusted under 35 U.S.C. 154(b) by 168 days.

(21) Appl. No.: 17/191,996

(22) Filed: Mar. 4, 2021

(65) Prior Publication Data

US 2021/0275485 A1    Sep. 9, 2021

Related U.S. Application Data

(60) Provisional application No. 63/100,221, filed on Mar. 4, 2020.

(51) Int. Cl.

| | | |
|---|---|---|
| *A61K 31/202* | (2006.01) | |
| *A61K 31/165* | (2006.01) | |
| *A61K 31/015* | (2006.01) | |
| *A61K 31/353* | (2006.01) | |
| *A61K 31/12* | (2006.01) | |
| *A61K 9/00* | (2006.01) | |
| *A61K 9/16* | (2006.01) | |

(52) U.S. Cl.
CPC .......... *A61K 31/202* (2013.01); *A61K 9/0014* (2013.01); *A61K 9/0053* (2013.01); *A61K 9/16* (2013.01); *A61K 31/015* (2013.01); *A61K 31/12* (2013.01); *A61K 31/165* (2013.01); *A61K 31/353* (2013.01)

(58) Field of Classification Search
CPC ... A61K 31/015; A61K 31/165; A61K 31/202
See application file for complete search history.

(56) References Cited

FOREIGN PATENT DOCUMENTS

| WO | WO-2011027373 A1 * | 3/2011 | ............. A61K 31/05 |
|---|---|---|---|
| WO | WO-2012104706 A1 * | 8/2012 | ........... A61K 31/015 |
| WO | WO-2019197967 A1 * | 10/2019 | ........... A61K 31/015 |

OTHER PUBLICATIONS

Seol et al. Korean J. Anesthesiol., Oct. 2017 70(5): 561-566 (Year: 2017).*
Petrosino et al. Front. Pharmacol. Mar. 2018, 9:249, 17 pages (Year: 2018).*
Fotio et al. Front. Pharmacol. Jun. 2019, 10:711, 11 pages (Year: 2019).*
D'Amico et al. Int. J. Mol. Sci. 2020, 21, 5330, 27 pages (Year: 2020).*

\* cited by examiner

*Primary Examiner* — James D. Anderson
(74) *Attorney, Agent, or Firm* — Nath, Goldberg & Meyer; Joshua B. Goldberg

(57) ABSTRACT

Compositions and methods for prophylactically sustaining and/or maintaining a robust endocannabinoid system in patients for modulating excess inflammatory response and inflammatory diseases over the mammalian lifespan to mitigate age-related discomfort. Specifically, a method of treating inflammatory and neuropathic pain in a mammal by administering a synergistic pharmaceutical daily dosage form comprising: palmitoylethanolamide (PEA), beta-caryophyllene (BCP) and docosahexaenoic acid (DHA).

18 Claims, No Drawings

COMPOSITION OF ACTIVE AGENTS TO POSITIVELY AFFECT A ROBUST MAMMALIAN ENDOCANNABINOID SYSTEM TONE TO BETTER ADDRESS AGE RELATED DISCOMFORT

This application claims priority to U.S. Provisional Patent Application Ser. No. 63/100,221, filed on Mar. 4, 2020, the contents of which are incorporated herein by reference in their entirety.

BACKGROUND

Field

The present subject matter relates to compositions and methods for prophylactically sustaining and/or maintaining a robust endocannabinoid system in patients for modulating excess inflammatory response and inflammatory diseases over the mammalian lifespan to mitigate age-related discomfort.

Description of the Related Art

Persistent pain in neuropathic conditions is often quite refractory to conventional analgesic therapy, providing most patients with only partial, if any, symptomatic relief.[29] Chronic pain is a frequent condition calling for improved analgesics, affecting an estimated 20% of people worldwide.[25,24] Treatment of such complex pains with one or a combination of two analgesics at the most is typical, although generally inadequate.[26,31]

Cannabinoids are scientifically recognized as natural anti-inflammatory compounds with superior efficacy versus NSAIDs (nonsteroidal anti-inflammatory drugs that decrease pain[34] and lower fever, and, in higher doses, decrease but without well-known negative side effects of long term use which includes risk of gastric ulcers, including recent meta-analysis showing potential increased risk of coronary heart disease.[35,44] But as a result of various life stresses, both internal and external to living mammals over the lifespan, the eCS can become less efficient due to diminished performance of any and/or all of the eCS components.[36] Such diminished eCS performance can lead, through inefficient homeostasis, to poor wellness over the lifespan.[36]

Diminished homeostasis leads to increased inflammation which can result in damaged tissues, nerves and joints, often associated with age related discomfort. Chronic conditions of diminished eCS performance from life stresses, illnesses and aging has been defined as Clinical EndoCannabinoid Deficiency (CECD). Several otherwise unexplained conditions including migraine, irritable bowel syndrome and fibromyalgia have been attributed to CEDC.[36,37,41a]

The NIH has patented CBD (CannaBiDiol) for its anti-oxidant and anti-inflammatory properties.[37a] Subsequent research has established CBD as an effective anti-inflammatory phytocannabinoid compound for use in pain mitigation related to tissue damage typically due to inflammation in mammals. CBD is also known to help sustain a robust system-wide endoCannabinoid (eCB) System Tone based on optimal performance of the various components of the "classic" endocannabinoid system (eCS) (i.e., cannabinoid receptors $CB_1$ and $CB_2$, the eCB neurotransmitter ligands AEA and 2-AG, and their metabolic enzymes FAAH or MAGL).[39,39a]

Cannabis as a genus was classified by the US DEA (Drug Enforcement Administration) as a Class 1 Controlled Substance. 'Marijuana', the Cannabis plant family with flowers containing naturally significant quantities of THC (TetraHydroCannabinol) and nominal amounts of CBD. Hemp plants (legally classified as Industrial Hemp) have naturally significant amounts of CBD but only trace amounts of THC (<0.3% by dry weight). This over-reaching DEA classification of all of Cannabis instead of only THC/Marijuana, has caused a hopelessly confusing condition regarding CBD legality resulting in tightly controlled limits on CBD research as well as lack of federal regulations required to insure FDA product safety labeling. Because of the many positive wellness related effects of CBD acting on the endoCannabinoid System (eCS), CBD has attracted considerable attention and interest from the general public. The key influence of CBD is on the signaling process of homeostasis that maintains physiological/biochemical balance in all living mammals.[40]

All vertebrate animals have an endocannabinoid system (eCS). In fact, the eCS is ubiquitous in nearly all animals from mammals to the more primitive phyla such as Cnidaria; the early emergence of the eCS in the evolution of the Phyla, indicates its biological importance. The eCS, providing homeostatic balance to the nervous, immune, and many other organ systems, opened the door to novel approaches targeting many conditions including pain management and inflammatory diseases. The eCS consists of three parts: (1) endogenous ligands, (2) G-protein coupled receptors (GPCRs), and (3) enzymes to degrade and recycle the ligands. Three endogenous cannabinoid molecules have been identified as ligands in the ECS to date: anandamide (ANA or arachidonoylethanolamide), 2-AG (2-arachidonoyl glycerol) and PEA (palmitoylethanolamide). Two G-coupled protein receptors (GPCR) have been described, with others being considered. Coincidentally, the phytochemicals are produced in large quantities by the Cannabis sativa L plants (predominantly CBD in Hemp and predominantly THC in Marijuana). These plant-based cannabinoids (termed phytocannabinoids) can interact with this system as ligands.[33,33a]

The eCS is a biological signaling system involved in regulating the physiological and biological balancing processes (homeostasis) in all mammals. Furthermore, the eCS is essential to CNS homeostasis and plays a significant role in the regulation of the inflammatory processes and pain signaling.[41] The endocannabinoid system has been shown to have a homeostatic role (i.e., homeostasis, the state of steady internal biochemical balance conditions maintained in all healthy mammals) by controlling several metabolic functions, such as energy storage and nutrient transport.[41] This dynamic state of equilibrium management concerning the constancy of the internal environment in which the cells of the body live and survive is the condition of optimal functioning for the organism including but not limited to variables, such as body temperature and fluid balance, being kept within certain pre-set limits (homeostatic range). Other variables include the pH of extracellular fluid, the concentrations of sodium, potassium and calcium ions, as well as that of the blood sugar level all needing to be regulated despite changes in the environment, diet, health, or level of activity.[41]

Each of these variables is controlled by one or more regulators or homeostatic mechanisms, which together maintain the living organism. Optimum health and wellness depends on robust operational tone of the eCS to regulate homeostasis throughout the mammalian lifespan. Disruption of homeostasis due to excess stress, disease, aging or other conditions of modern life can result in reduced eCS performance or poor eCS tone, yielding various age related discomforts in which pain is typically involved.[41] Certain painful conditions have been positively associated with Clinical EndoCannabinoid Deficiency (CECD). An emerging literature documents the CECD syndrome as an etiology in migraine, fibromyalgia, irritable bowel syndrome, psychological disorders, and of other illnesses and conditions potentially contributing to various additional age related discomforts.[37]

The best-known natural endogenous or endocannabinoids are anandamide (ANA), 2 acyl-glycerol (2AG) and palmitoylethanolamide (PEA). These naturally produced bioactive lipids are capable of interacting directly or indirectly with the endocannabinoid receptors such as $CB_1$ and $CB_2$, the activation thereof is responsible for different properties including, but not limited to, anti-inflammatory, antioxidant and analgesic properties. These receptors are sensitive to endogenous cannabinoids, as well as phytocannabinoid compounds derived from plants and/or cannabinoids of synthetic derivation, that belong to receptors coupled to protein G.[46]

$CB_1$ and $CB_2$ receptors are structurally similar. $CB_1$ receptors are abundant in the central nervous system, particularly the hippocampus and associated cortical regions, in the brain and in the basal ganglia. $CB_2$ receptors are abundant in the peripheral nervous system mostly associated with the immune system being primarily present in T cells, the mastocytes, B lymphocytes and at the level of the hematopoietic cells as well as in the peripheral nervous terminations, playing an important role in the antinociceptive, antalgic and anti-inflammatory activity. Endocannabinoids of natural origin, including PEA, represent an important alternative to the traditional anti-inflammatory drugs treating inflammation (neuroinflammation or other types of inflammatory conditions) and in all conditions characterized by painful symptomatology.[40]

CBD and THC are natural phytocannabinoid compounds in *Cannabis* (plant families commonly known as Marijuana and Hemp). CBD and THC are mammalian CB (cannabinoid) receptor agonists that have been used to reduce pain in humans for millennia. But THC causes 'intoxication' and its use and research into its mechanism of action have been severely limited by the Drug Enforcement Administration (DEA) listing of *Cannabis*, including CBD, as a continuing Class 1 Controlled Substance for many decades.[50] And recent studies indicate potential damage to the fetus of pregnant women using CBD, especially inauthentic CBD oils.[38]

Because CBD is now an FDA approved drug (i.e., CBD isolate known as Epidiolex® for pediatric seizures) and other *Cannabis* derived phytocannabinoids (i.e., THC) are currently entangled in State and Federal legal issues, alternative approaches to maintaining robust eCS tone functioning into old age are needed and desirable.

Given the redundancy and complex nature of the underlying pathogenesis, where multi-modal, alternative pathways including a variety of receptors, neurotransmitters and regulatory systems are involved in the pain process, new approaches involving redundancy of multimodal alternative pathways simultaneously involved in the pain mitigation process, are logically justifiable as a unique approach.[32] The present subject matter addresses these needs.

SUMMARY

This present subject matter addresses a prophylactic approach to mitigating age-related discomfort from increased chronic inflammation due to a weakened endocannabinoid system's inability to robustly regulate homeostasis. Homeostasis is how the mammalian body actively regulates all biological systems to maintain a confined range of optimum conditions—consistently, even during sleep. Homeostasis is typically maintained through negative feedback signals only when something changes and the body begins to correct itself. The endocannabinoid system (eCS) plays an essential regulatory role in that correction.[40]

In one embodiment, the present subject matter relates to a method of treating inflammatory and neuropathic pain in a mammal comprising:

administering to a mammal in need thereof a synergistic pharmaceutical daily dosage form comprising: palmitoylethanolamide (PEA) in an ultramicronized form, beta-caryophyllene (BCP) and docosahexaenoic acid (DHA) in liquid form;

wherein the palmitoylethanolamide (PEA), beta-caryophyllene (BCP) and docosahexaenoic acid (DHA) are contained in the daily dosage form in doses not exceeding about 1200 mg/day of the palmitoylethanolamide (PEA), not exceeding about 0.1 mL/kg of beta-caryophyllene (BCP), and not exceeding about 10 mg/kg of docosahexaenoic acid (DHA);

wherein the pharmaceutical daily dosage form has palmitoylethanolamide in a weight percentage between about 1 and about 2%, beta-caryophyllene (BCP) in a weight percentage between about 10 and about 30% and docosahexaenoic acid (DHA) in a weight percentage between about 10 and about 30%.

In another embodiment, the present subject matter relates to a method of treating neuropathic and inflammatory pain in a mammal, comprising: administering to a mammal in need thereof a dosage form selected from the group consisting of a chew, tablet, capsule, or a liquid form of a synergistic pharmaceutical composition, wherein each dosage form of the pharmaceutical composition comprises: palmitoylethanolamide in a weight percentage between about 1 and about 2%, beta-caryophyllene (BCP) in a weight percentage between about 10 and about 30% and docosahexaenoic acid (DHA) in a weight percentage between about 10 and about 30% and one or more compounds with anti-inflammatory activity in a total weight percentage ranging between 0 and about 20%.

DETAILED DESCRIPTION OF THE PREFERRED EMBODIMENTS

It is noted that, as used in this specification and the appended claims, the singular forms "a", "an", and "the" include plural references unless the context clearly dictates otherwise.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to compositions of matter and methods of preparation comprising non-*Cannabis* derived, biologically diverse active agents, specifically including palmitoylethanolamide (PEA), the endogenous cannabinoid, docosahexaenoic acid (DHA), an omega 3 fatty acid, and beta-caryophyllene (BCP), the cannabinoid-like terpene. The compositions of the present subject matter may also include any and all additional plant components including but not limited to cannabinoids, (including, but not limited to, cannabichromine (CBC), cannabigerol (CBG), cannabidiol (CBD), and cannabidiolic acid (CBDA)), terpenes, (including, but not limited to, humalene, myrcene, linalool, and pinene) and other herb and plant-based components (including but not limited to wintergreen, capsaicin, and chlorophyllin), that employed over the mammalian lifespan, can modulate inflammatory diseases in order to mitigate age-related discomfort. Depending on application various herbs and flavonoids (including, but not limited to, quercetin, curcumin and green tea extracts) as well as certain excipients (including, but not limited to, dimethylsulphoxide and silicon dioxide) may also be incorporated into the composition. These composition components are intended to positively affect the functioning of the mammalian endocannabinoid system (eCS) subject to functional weakness due to loss of robust eCS tone, resulting in increased lifespan inflammation response and increased age-related discomfort.

At the center of age-related discomfort is pain, commonly resulting from tissue and/or nerve damage typically due to chronic immune system inflammation. Chronic pain lasts or recurs for more than 3 to 6 months persisting past normal healing time. Chronic pain is a frequent condition calling for improved analgesics, affecting an estimated 20% of people worldwide. Pain perception depends on signaling to and from the brain involving a well-functioning, robust endo-Cannabinoid System (eCS). The eCS is the key to regulating homeostatic signaling (including down-regulation of pain signals) throughout the mammalian body and brain including immune system inflammatory response. The eCS can lose its robust tone due to stresses of life and aging resulting in greater incidence of excess or chronic inflammation over the lifespan and thereby increasing tissue damage and accompanying pain or age-related discomforts.

Different naturally occurring Cannabinoids are found in plants (i.e., phytocannabinoids) and within mammals (i.e., endocannabinoids) but all are active neurotransmitters involving the mammalian eCS. These cannabinoids are known to interact synergistically in diverse entourage groups involving various neurotransmitter receptors with a variety of similar compounds including, but not limited to, cannabinoids, terpenes, flavonoids, and terpenoids to produce a more powerful 'entourage' effect than when individually acting alone. When functioning properly, natural endogenous cannabinoids (endoCannabinoids), including but not limited to AEA, 2AG and PEA, are the basis for maintaining a functionally robust eCS tone in mammals.

When natural mammalian endocannabinoid production is inadequate for a variety of reasons (e.g., aging, stresses of living, certain illnesses, poor nutrition, etc.), plant derived 'phyto' cannabinoids (e.g., CannaBiDiol or CBD) can stimulate the components comprising the eCS to rejuvenate their functionality in order to achieve a more robust activity level or a more robust eCS tone. *Cannabis* derived CBD (and THC) are legally problematic due to their current federally controlled substance status. In contrast, the present subject matter in some embodiments can be a *Cannabis*-free composition to maintain a robust eCS tone across the patient's lifespan, thereby mitigating age-related discomfort.

BCP (Beta-Caryophyllene)

BCP (beta-caryophyllene) is one of the major active essential oil components of various spice and food plants (e.g., basil and cloves). Similar to CBD, BCP is a selective $CB_2$ Cannabinoid receptor agonist that has analgesic attributes. BCP's biological entourage effects include anti-inflammatory, anti-oxidative, and analgesic activities. Cannabinoid receptor agonists have shown therapeutic value against inflammatory and neuropathic pains, conditions that are often refractory to therapy. When activated, $CB_2$ receptors—expressed mainly by immune cells—can affect the release of chemical messengers (e.g., cytokines by immune cells) and can modulate immune cell trafficking. Activation of the $CB_2$ receptor is a potential therapeutic strategy for the treatment of inflammation, pain, atherosclerosis, and osteoporosis, all involved in age-related discomfort.[31a] For example, BCP's biological entourage effects include anti-inflammatory, anti-oxidative, and analgesic activities.[31,33,34]

DHA (Docosahexaenoic Acid)

*Cannabis* plants contain many components including seeds. Hemp seeds, for example, contain a significant amount of protective dietary n-3 polyunsaturated fatty acids (PUFA), particularly docosahexaenoic acid (DHA). This fact leads to the surprising conclusion that DHA has provided survival characteristics to the *Cannabis* plant. A carrier component of many commercially available CBD oils, DHA is a widely available G.R.A.S. nutritional supplement from non-*Cannabis* sources such as pure powder form in algae and in fish oil. DHA, a unique fatty acid that significantly alters basic properties of cell membranes, is an important modulator of a mammalian host's inflammatory/immune responses. For example, DHA can attenuate pro-inflammatory cytokines for the treatment of autoimmune and chronic inflammatory diseases. For these, and other, reasons, DHA can be included with BCP and PEA in the present compositions.

PEA (Palmitoylethanolamide)

The presence of PEA (and other structurally related N-acylethanolamides) has been known to enhance anandamide activity by an "entourage effect" whereby the complex system of receptors and ion channels responding to a variety of neurotransmitters, including but not limited to cannabinoids, terpenes, flavonoids, fatty acid amides, lipids, etc.[7] PEA's analgesic and anti-inflammatory mode of action is by activating a nuclear receptor, the Peroxisome Proliferator-Activated Receptor alpha (PPAR-alpha), a master-switch for a great number of genes activating inflammatory cascades. In other word, PEA resets over-active genes, which code for inflammation.[3a] Therefore, PEA in conjunction with other terpenoid/cannabinoid compounds including but not limited to BCP and essential oils including DHA, described herein, can result in a boosting of eCS performance for a robust eCS tone in order to prophylactically minimize future age related discomforts. Just as there are a multitude of components (e.g., compounds, enzymes, ion channels, neurotransmitters, etc.), involved in the processing of pain, the contemporary use of the several primary active compounds described herein show an unexpectedly significant synergistic effect on hyperalgesia and neuropathic pain with respect to the single active ingredients acting alone.[28a]

PEA is a fatty acid amide endocannabinoid discovered in 1957 in egg yolks that prevented rheumatic fever when fed to poor children with known streptococcal infections. Subsequently, PEA was found to alter the course of influenza.[3] PEA is synthesized by healthy tissue in the human body in response to inflammation.[4] It works as a signaling molecule to down-regulate the inflammatory response of glial cells and mast cells. PEA is made by various plants and animals and is present throughout the animal kingdom. It can be extracted from natural sources, but modern production methods typically synthesize it from palmitic acid. PEA, available as a nutraceutical supplement, with a significant number of prospective and randomized trials demonstrating its pain-relieving effects with no reported drug-drug interactions and very few reported adverse effects from PEA.[3] PEA has been studied in in vitro and in vivo systems using exogenously dosed compound with evidence that it binds to the peroxisome proliferator-activated receptor alpha (PPAR-$\alpha$)[5] through which it exerts a variety of biological effects, some related to chronic inflammation and pain.[6,7]

In addition to the peroxisome proliferator-activated receptor alpha (PPAR-$\alpha$),[5,6,8] PEA also has affinity to cannabinoid-like G-coupled receptors GPR55 and GPR119.[9] While PEA lacks complete affinity for the CB1 and CB2 cannabinoid receptors,10 primary research supports that the presence of PEA enhances anandamide activity by an "entourage effect"[11,12] and that PEA levels are altered and that the endocannabinoid system (ECS) is "imbalanced" in acute and chronic inflammation.[13] PEA has been shown to have anti-inflammatory,[14] anti-nociceptive,[15] neuroprotective,[16] and anticonvulsant properties.[17]

PEA is a nutraceutical endocannabinoid that was retrospectively discovered in egg yolks. Feeding poor children with known streptococcal infections prevented rheumatic fever. Subsequently, it was found to alter the course of influenza. Since 2008, PEA, available from various foods (e.g., egg yolks, peanuts etc.,), has been available as a nutraceutical under the various brand names. A literature search on PEA has yielded over 350 papers, all referenced in PubMed, describing the physiologic properties of this endogenous modulator and its pharmacologic and therapeutic profile as an anti-inflammatory endocannabinoid.45 Palmitoylethanolamide targets nonclassical cannabinoid receptors rather than $CB_1$ and $CB_2$ receptors. Palmitoylethanolamide will only indirectly activate classical cannabinoid receptors by an entourage effect. There are a significant number of prospective and randomized trials demonstrating the pain-relieving effects of PEA. There are no reported drug-drug interactions and very few reported adverse effects from PEA.[3] The endocannabinoid Palmitoylethanolamide (PEA), a fatty acid amide discovered in 1957, has been studied in in vitro and in vivo systems using exogenously dosed compound with evidence that it binds to a nuclear receptor, the peroxisome proliferator-activated receptor alpha (PPAR-$\alpha$)[5] through which it exerts a variety of biological effects, some related to chronic inflammation and pain.[6,7]

PEA, a naturally occurring endocannabinoid not found in *Cannabis*, is associated with major effects in mitigating neuroinflammatory processes.[1] It is generally known that neuroinflammation has an important role in the causation and maintenance of chronic pain. This process is characterized by infiltration of immune cells, activation including granulation of mast cells and glial cells (as glial cells are emerging as a major factor in chronic pain), resulting in production of inflammatory mediators in the peripheral and central nervous system involving the eCS.[3,6] PEA is an anti-inflammatory and pro-resolving lipid mediator which controls glial and mast cell behaviors associated with pain. PEA down-modulates immune system mast cell activation response to tissue injury releasing inflammatory cytokines, NGF, histamines, and other molecules that attract white blood cells, thereby activating their nociceptor pathogen immune response.[19,49]

PEA induced pain relief is progressive, age- and gender independent. As an acylethanolamide, PEA readily disperses throughout different tissues in the body and brain, including nervous tissues.[6] Similar to ANA and 2AG, PEA is synthesized on demand when it's endogenous levels, systemic or local, are altered. This occurs in circumstances of stress, injury and/or pain. PEA has no known acute or chronic toxicity nor significant side effects.[3]

PEA has a high efficacy/risk ratio, has no known tolerance effects, and does not interfere with concurrent therapies for pain or for co-morbid conditions. The effects of PEA are dose-dependent; long-term treatment with PEA has been shown to not only reduce pain but actually to preserve peripheral nerve function and mitigate brain inflammation.[3] Supplemental PEA, as a natural endocannabinoid, has capabilities to increase the robustness of the eCS as other cannabinoids (endo- and phyto-) and therefore contribute prophylactically to reduction of age related discomfort. The effects of AEA and 2-AG can be enhanced by "entourage compounds" such as N-palmityletanolamide (PEA) that inhibit their hydrolysis via substrate competition, and thereby prolong their action.[1]

A main target of PEA is the peroxisome proliferator-activated receptor alpha (PPAR-$\alpha$).[5,8] PEA also has affinity to cannabinoid-like G-coupled receptors GPR55 and GPR119.[9] While PEA lacks complete affinity for the $CB_1$ and $CB_2$ cannabinoid receptors $CB_1$ and $CB_2$,[10] primary research supports that the presence of PEA enhances anandamide activity by an "entourage effect".[11,12,28a] Primary research supports the conclusion that PEA levels are altered and that the endocannabinoid system (eCS) is "imbalanced" in acute and chronic inflammation.[13] PEA has been shown to have antiinflammatory,[14] anti-nociceptive,[15] neuroprotective,[16] and anticonvulsant properties.[17]

The present subject matter relates to a unique composition of matter including BCP, DHA and a naturally occurring CB receptor agonist so-called 'super-cannabinoid", PEA nutritional supplement available from natural non-*Cannabis* sources. PEA is able to perform the function of maintaining a robust eCS tone in a similar way to that of CBD.

Maintenance of a robust endocannabinoid system (eCS) functionality or 'tone' across a mammal's lifespan is supported by cannabinoid supplementation.[1] Legal and regulatory issues make use of the cannabinoid entourage effect from *Cannabis* problematic.[2] The present subject matter eliminates the issues surrounding *Cannabis* by completely avoiding any involvement of *Cannabis* derived compounds. This subject matter is based on a little-known non-*Cannabis* derived cannabinoid, Palmitoylethanolamide (PEA).

PEA, in combination with two other natural generally recognized as safe (GRAS) compounds, BCaryoPhyllene (BCP) and DocosaHexaenoic Acid (DHA), and at least one other anti-inflammatory compound, describes a unique composition of matter.[18] The composition mimics the eCS entourage effect of *Cannabis* in support of a robust eCS tone necessary for effective, robust regulation of homeostasis for anti-inflammatory balance without relying on CBD (CannaBiDiol) or any other *Cannabis* derived compounds such as THC.[19] The objective is to maintain a robust eCS tone necessary to properly regulate homeostasis in order to keep inflammation in balance, thereby minimizing chronic inflammation, over the lifespan and therefor reduce potential for age-related discomfort in living mammals.[20,40a]

The present subject matter relates to compositions and methods of preparation comprising the non-*Cannabis* derived biologically diverse active agents palmitoylethanolamide (PEA), an endogenous cannabinoid, docosahexaenoic acid (DHA), an omega 3 fatty acid, beta-caryophyllene (BCP), a cannabinoid-like terpene, and any plant components including but not limited to cannabinoids, terpenes, flavonoids, and terpenoids, including but not limited to cannabichromine (CBC), cannabigerol (CBG), cannabidiol (CBD), cannabidiolic acid (CBDA), humalene, myrcene, linalool, and pinene, intended to positively affect the functioning of all mammalian endocannabinoid systems subject to functional weakness resulting in age related discomfort.[1,29] At the center of age related discomfort is pain, typically resulting from tissue and/or nerve damage due to immune system inflammatory response.[21] Chronic pain lasts or recurs for more than 3 to 6 months[22] persisting past normal healing time.[23] Chronic pain is a frequent condition calling for improved analgesics, affecting an estimated 20% of people worldwide.[24,25,26] Pain perception depends on signaling to and from the brain and a well functioning endocannabinoid system (eCS), the key to regulating homeostatic signaling throughout the mammalian body and brain.[27]

These cannabinoids interact synergistically in a diverse entourage of groups with a variety of similar compounds including, but not limited to, terpenes to produce greater 'entourage' effects than when individually acting alone. Naturally occurring Cannabinoids are active through the eCS in all living mammals. The effects of AEA and 2-AG can be enhanced by "entourage compounds" that inhibit their hydrolysis via substrate competition, and thereby prolong their action. Entourage compounds includes N-palmityethanolamide (PEA).[1]

When functioning properly, natural endogenous cannabinoids (endoCannabinoids), including but not limited to AEA, 2AG and PEA, are the basis for maintaining a functionally robust eCS tone.[28] When natural mammalian endocannabinoid production is inadequate for a variety of reasons (e.g., aging, stresses of living, certain illnesses, poor nutrition, etc.), plant derived 'phyto' cannabinoids (e.g., CannaBiDiol or CBD) can stimulate the components comprising the eCS to increase their number and rejuvenate their functionality in order to achieve a more robust activity level or a more robust 'eCS tone'.[29] beta-CaryoPhyllene (BCP), a terpene produced in a wide variety of non-*Cannabis* plant sources, is a Cannabinoid receptor agonist that interacts with various receptors, including but not limited to, $CB_2$, much the same way as CBD. When activated, $CB_2$ receptors—expressed mainly by immune cells—can affect the release of chemical messengers (i.e., cytokines by immune cells) and can modulate immune cell trafficking.[30] Activation of the $CB_2$ receptor is a potential therapeutic strategy for the treatment of inflammation, pain, atherosclerosis, and osteoporosis.[31]

The presence of PEA (and other structurally related N-acylethanolamides) has been known to enhance anandamide activity by an "entourage effect" whereby the complex system of receptors and ion channels responding to a variety of proximal neurotransmitters, including but not limited to cannabinoids, terpenes, flavonoids, fatty acid amides, lipids, etc.[27,27a] Therefore, PEA in conjunction with other terpenoid/cannabinoid compounds including but not limited to BCP described herein can result in a boosting of eCS performance for a robust eCS tone in order to prophylactically minimize future age related discomforts through, for example, reduction of chronic inflammation. Just as there are a multitude of components (e.g., compounds, enzymes, ion channels, neurotransmitters, etc.), involved in the processing of pain, the contemporary use of the several primary active compounds described herein show an unexpectedly significant synergistic effect on hyperalgesia and neuropathic pain with respect to any single active ingredient acting alone.[28a]

Inflammation & Natural Herbs

The incidence of diseases with inflammatory etiopathology have recently increased. Drugs relieving these ailments also produce serious life threatening consequences. Research on medicinal herbs and the endocannabinoid system have opened a new era in the prophylactic and therapeutic management of inflammatory diseases. Medicinal plants or their constituents are considered beneficial due to satisfactory potency, ease of availability, cost effectiveness, much less or no side effects, safer and efficient as compared to synthetics. Natural products including medicinal herbs containing phytoconstituents can prevent undesirable inflammatory processes and posses anti-inflammatory activity.[40] Inflammation is part of the complex biological response of body tissues to harmful pathogens, damaged cells, or irritants, and is a protective response involving immune cells, blood vessels, and molecular mediators. The inflammatory response is designed to eliminate the initial cause of cell injury to help fight and clear necrotic cells, and repair damaged tissue and organ systems. Too little inflammation can lead to progressive tissue destruction by the harmful stimulus (e.g. bacteria) potentially compromising organism survival. Although this process is protective, the failure to resolve the inflammation and return the target tissue to homeostasis can result in chronic inflammation. Chronic inflammation is associated with various autoimmune and chronic inflammatory diseases such as rheumatoid arthritis, inflammatory bowel disease atherosclerosis, including the promotion of cancer.[47]

Vitamin B

In other embodiments, the present methods and compositions can further include one or more B vitamins, or B-complex vitamins. The inclusion of such B vitamins may be of particular assistance in treating chronic inflammation and age-related discomforts generally.

Since the late 1980s, the role of B vitamins on analgesia have been a topic of research.[65] All B vitamins have important roles as coenzymes and precursors for enzymatic reactions in different biological systems.[66] While these roles are different, they are related, and all B vitamins as discussed herein can be considered individually or grouped together as "B-complex" vitamins.$_{68}$ Suitable, non-limiting examples of such B vitamins include thiamine (vitamin B1), pyridoxine (vitamin B6), and cyanocobalamin (vitamin B12). It is postulated that these vitamins, given at therapeutic doses (higher than physiologic replacement doses), alleviate pain when given alone, in combination, and as adjunct therapy alongside NSAIDs and other non-opiate analgesics. It is contemplated that when used in the present compositions, any of the B vitamins mentioned may have clinical roles including, but not limited to, the reduction of neuropathic pain, burning, and itching, inflammation, lower back pain, and postoperative discomfort. For example, these vitamins can potentially improve pain scores in conditions such as carpal tunnel, migraine, fibromyalgia, and premenstrual tension.$_{67}$ Such benefit from B-vitamin supplementation may result from the correction of underlying deficiencies, as well as direct analgesic and antinociceptive action throughout the body, and especially in the peripheral nervous system.$_{70}$ B complex vitamins do not only contribute to important physiological functions as co-factors, antioxidants, and structural components in the whole human body, but they also possess neurospecific functions.$_{69}$ More recently, these vitamins have been found to, at times, inhibit the nociceptive activity in neurons found in the dorsal horn of the spinal cord and in the thalamus.$_{71}$ As evidenced by decreased C-reactive protein serum levels found in patients with B-complex supplementation as well as B12 monotherapy, these vitamins could play a direct role in systemic inflammation.$_{72}$ B vitamins are not made in the mammalian body and must be ingested. Even with a well-balanced diet, Thiamine (B1) can be obtained from dairy, whole grain, and red meat and recommended dietary dosage is about 1.2 mg/day, although therapeutic doses of up to 750 mg/day have been studied and are regarded as safe.$_{68}$ Pyridoxine (B6) sources include fish, beef liver, starchy vegetables, and non-citrus fruits. Recommended daily dosage of pyridoxine range from about 0.3 mg per day in infants, to about 1.7 mg per day in adults.$_{73}$ While B vitamins are water soluble and easily excreted, extremely high doses of pyridoxine over time are associated with various acute and chronic neuropathies. Pharmacologic doses of pyridoxine shown to provide analgesic benefits range between about 5 and about 50 mg per day. Cyanocobalamin (vitamin B12) and its "activated" form, methylcobalamin (methyl-B12), are popular supplements and well known for their clinical roles in neuropathic pain. Dietary sources of vitamin B12 include fish, meat, poultry, eggs, and dairy. Recommended daily intake is between about 0.5 and about 2.4 mcg/day for children and adults, respectively, while therapeutic doses ranging from about 0.3 mg to about 10 mg per day may be safe and effective in various pain models and as adjunct therapy for inflammatory pain.$_{68}$ Herbs and Phyto-Supplements
DHA (Docosahexaenoic Acid)

Much published literature supports the contention that dietary n-3 polyunsaturated fatty acids (PUFA), docosahexaenoic acid (DHA) in particular, is an important modulator of a host's inflammatory/immune responses and for the treatment of autoimmune and chronic inflammatory diseases.$_{42}$ DHA (docosahexaenoic acid) is a unique fatty acid, because it significantly alters basic properties of cell membranes, including fatty acid chain order and fluidity, phase behavior, elastic compressibility, ion permeability, fusion, rapid flip-flop, and resident protein function.$_{43}$ BCP (Beta-Caryophyllene)

beta-caryophyllene (BCP), a phytocannabinoid from various non-*Cannabis* sources is Generally Recognized as Safe (GRAS) and FDA approved for food use. BCP selectively binds to the $CB_2$ receptor, acting as a strong $CB_2$-selective agonist. $CB_2$ activation can mediate anti-nociception either directly or indirectly by inhibiting IL-1beta and TNF-α; TRP-1, TRP-2, NO, IL-1beta, IL-6, IL-8, IL-12. IL-17, where direct activity is exerted through $CB_2$ stimulation on primary sensory neurons.$_{56}$ BCP displays similar analgesic activities as several essential oils, in which BCP is a major active compound (e.g., basil and rosemary). One can hypothesize that better analgesic effects may be obtained when BCP is used in combination with other natural agents of desired properties. In inflammatory hyperalgesia, indirect pain inhibition through $CB_2$ localized on mast and immune cells is possibly achieved by the reduction of prostanoids or cytokines release, which are responsible for peripheral nociceptor sensitization that tissue damage leading to a painful feeling, is occurring. BCP inhibits proinflammatory cytokine expression in peripheral blood. One can hypothesize that better analgesic effects may be obtained when BCP is used in combination with other natural agent(s) of desired properties. As a photo-cannabinoid, BCP may act in a similar manner to other $CB_2$-selective agonists. $CB_2$ activation can mediate anti-nociception either directly or indirectly, where direct activity is exerted through $CB_2$ stimulation on primary sensory neurons. In inflammatory hyperalgesia, indirect pain inhibition through $CB_2$ localized on mast and immune cells is possibly achieved by the reduction of prostanoids or cytokines release, which are responsible for peripheral nociceptor sensitization.$_{34}$ Cannabinoids and the Endocannabinoid System The eCS homeostatic control mechanism is composed of endocannabinoids, which are endogenous lipid-based retrograde neurotransmitters that bind to or impact various cannabinoid receptors, and cannabinoid receptor enzymes expressed throughout the vertebrate central nervous system including the brain and peripheral nervous system. The "classic" endocannabinoid system (eCS) includes the primary cannabinoid receptors $CB_1$ and $CB_2$, the eCB neurotransmitter ligands anandamide (AEA), 2-arachidonoylglycerol (2-AG) and palmitoylethanolamide (PEA) and their metabolic enzymes including fatty acid amide hydrolase (FAAH) or monoacylglycerol lipase (MAGL), responsible for just-in-time synthesis and degradation of the receptors needed in maintaining homeostasis for proper health and wellness. Wellness is when physiological processes and systems are functioning properly so that everything is 'in balance.' Homeostasis is the process of maintaining this complex system-wide balancing act near physiological balance necessary for lifespan health and wellness Inflammation is a far from homeostasis condition designed to repair minor imbalances while chronic inflammation is a health disruptor.$_{28}$ The CECD syndrome can occur when the eCS loses its robust tone and is unable to maintain homeostasis thereby allowing inflammation to support various disorders, illnesses and conditions potentially contributing to various additional age related discomforts.$_{37}$ A systematic review of clinical interventions that enhance the operational performance of the eCS, (i.e., ways to up regulate cannabinoid receptors, increase ligand synthesis, or inhibit ligand degradation) identifies the phytocannabinoid cannabidiol (CBD)—an analog of the endocannabinoid 2AG—as an efficacious natural compound of *Cannabis* plants able to maintain a robust eCS tone (a measure of eCS ability to do its job efficiently.) Currently, however, CBD along with all other *Cannabis* derived phytochemical compounds are guilty by association with tetrahydrocannabinol (THC) the only component of *Cannabis* (i.e., marijuana and hemp plant families) with potentially harmful psychological effects including intoxication and potential brain damage with continuous and/or high levels of ingestion and/or inhalation.$_{26}$ The drug Epidiolex (containing 95% CBD) has been approved by the FDA to treat pediatric seizures (i.e., Lennox-Gastaut and Dravet syndromes). Because CBD is now a drug, FDA is enabled to further limit the casual use of CBD for treating any health condition without FDA approval, requiring a costly and time consuming gold standard clinical trial process for each indication.$_{21}$ Alternative *Cannabis*-derived cannabinoids are available to potentially maintain eCS tone. However, these compounds are also associated with the legal restrictions on *Cannabis* and so are currently impractical as candidates for classification as 'generally recognized as safe'(GRAS). The present subject matter describes a novel and unexpected combination of at least some Non-*Cannabis* derived cannabinoids, terpenes, fatty acids and other nutritional supplements in combination able to safely maintain a robust eCS tone promoting regulation of inflammation and reduced pain signaling to prevent at best and mitigate at worst Age Related Discomfort.

The literature describes common over the counter compounds including various typically used NonSteroidal Anti-Inflammatory Drugs (NSAIDs) (e.g., aspirin, Advil, Celebrex, ibuprofen (Motrin), naproxen (Aleve, Naprosyn), etc.) that relieve pain and reduce inflammation. However, over the counter NSAIDS, although legal, cause recently described long term effects in addition to common short term nausea, vomiting, diarrhea, constipation, rash, headache and bleeding. Cannabinoids are scientifically recognized as natural anti-inflammatory compounds with superior efficacy versus NSAIDs without their long term use effects which includes risk of gastric ulcers and potential increased risk of coronary heart disease.$_{35,44}$ Furthermore, NSAIDs do not maintain the critical robust eCS tone condition that cannabinoids do. Cannabinoids interact with the eCS to reduce inflammation and down-regulate related pain without serious side effects. Until CBD and other *Cannabis* derived compounds are federally regulated and legal according to the FDA, FTC and DEA, they are problematic as nutritional supplements.$_{48}$ In future, the present compositions may possibly further include *Cannabis* derived compounds when they are no longer listed as Class 1 controlled substances.$_{48}$ The science of the endocannabinoid system is relatively new and not yet taught in medical/veterinary schools. In addition, the pharmacology of *Cannabis* plants is not well understood because of its prohibition as a class one controlled substance which tightly restricted plant material for US research. As such, the more than 100 phytocannabinoids and over 200 terpenes included in *Cannabis* plants are still not well understood.$_{14}$ A limited number of terpenes from a variety of non-*Cannabis* plants have been used primarily as fragrances in cosmetics as well as in aroma therapy. They are not discussed in relation to the eCS. DHA, commonly known as fish oil, is recommended by doctors for maintaining cardiovascular health, especially controlling triglycerides implicated in arteriosclerosis.

The present subject matter describes non-obvious combinations of certain natural non-*Cannabis* derived compounds (and their methods of preparation) including but not limited to N-acetylethanolamides/cannabinoids (e.g., palmitoylethanolamide or PEA) possessing significant analgesic properties through eCS regulated homeostasis including, but not limited to, down regulation of noception and pain which is common to age-related discomfort in humans and companion animals. Over the mammalian lifespan, maintenance of a more robust eCS tone will reduce unnecessary chronic inflammatory response. Maintenance of a robust eCS tone will result in reduced inflammatory disease implicated in chronic tissue damage, for example, and therefore reduced age-related discomfort.

The repeated frustration of not being able to use CBD from Hemp oil in companion animals and humans in competitive sports resulted in a search for a new composition of matter that acted on the eCS like Hemp oil (with its hundreds of components) acting together in a coordinated entourage effect on the process of homeostasis regulation.$_{27}$ After serious effort to identify the various receptors involved in pain, the operation of the eCS and then researching the various components of *Cannabis* to find a terpene that was able to act like CBD but not be from *Cannabis* did the molecule known as BCP was identified. Finally, a third primary component with influence in the inflammatory process was inferred from the chemistry of hemp seed oil rich in DHA. There is nothing obvious in the literature that connected these three components acting together especially not involving the eCS or inflammation.$_{8,53}$ A robust eCS tone effect is obtained by administering several anti-inflammatory and or antioxidant compounds in combination with PEA (PalmitoylEthanolAmide) including DHA (DocosaHexaenoic Acid) and BCP (Beta-CaryoPhyllene) at the same time, at particular dosages and in combination with various analgesic/anti-inflammatory ingredient/excipients examples of which are listed in Table 1. Stated another way, the contemporary use of the three active compounds (i.e., PEA, DHA and BCP) in specific combination shows an unexpected synergistic effect on hyperalgesia and neuropathic pain with respect to the single active ingredients administered alone.$_{42,28}$ Depending on formulation and modes of administration in mammals, the present subject matter can systemically enhance eCS tone which may reduce inflammatory pain through 1. the eCS and 2. other pain associated cell receptors and pathways including, but not limited to, $CB_1$, $CB_2$, GP65, TRPV1/2, PPAR-α activation as well as, mast cells and glial cells throughout the mammalian brain and body.$_{6,45,51}$ In addition to conventional eCS receptors, other associated cell receptors including but not limited to inhibitors, receptor signaling modulators (e.g., aminos acids, lipids, peptides/proteins, etc.) as well as others and non-receptor modulators (e.g., glial and mast cells), including but not limited to, ion channels and transporters located throughout mammalian brain/body physiology believed to impact issues such as pain associated with age related discomfort.$_{13,29}$ Additional additives, including but not limited to, polyunsaturated fatty acids (PUFAs) such as Omega 3 DHA (DocosaHexaenoic Acid), may be employed in enhancing the action of said anti-inflammatory and/or antioxidant compounds that would make it more effective in robust eCS tone maintenance.$_{54}$ Certain additional plant derived compounds with anti-inflammatory and antioxidant properties, including but not limited to Chlorophyllin, a liquid form of chlorophyll, will be useful in certain applications to make said composition more effective in eCS tone maintenance. Evidence has shown that chlorophyll has anti-inflammatory properties that may benefit those affected with chronic inflammation. In the journal Inflammation, researchers discovered that chlorophyll helped inhibit TNF-α (tumor necrosis factor-alpha) in mice. Chlorophyll supplements are generally considered safe in low doses, according to a 2014 study published in the Journal of Dietary Supplements.[55]

Various additives, including but not limited to, plant derived terpenes/terpenoids (e.g., betacaryophyllene (BCP)), that activate $CB_2$ receptors may be employed in enhancing the performance of said anti-inflammatory and/or antioxidant compounds (i.e., PEA and DHA) to increase effectiveness of a robust eCS tone in addressing age related discomfort.[5,43,56]

Natural plant flavonoids including, but not limited to, certain phenolic amides (e.g., capsaicin), may be useful in certain applications in reducing pain associated with age related discomfort.[57] Additional processing techniques including but not limited to ultrasonic cavitation in the generation of normally insoluble anti-inflammatory substances including, but not limited to, curcumin-loaded micelles. Such micelles could be employed to increase product aqueous solubility in addition to uniformity and efficacy which enables greater effectiveness in dealing with issues involved in age related discomfort.[58,59]

Various additives including, but not limited to, absorbent excipients such as silicon dioxide (i.e., colloidal silicon dioxide), can enable essential oils and aqueous solutions to be transformed into solids including but not limited to powders or rapid dissolving tablets for oral ingestion by mammals to facilitate bioavailability. Such excipients can also facilitate various dosage form manufacturing processes.[60]

In addition, the present compositions can be administered as a daily dosage form that is an oral or topical dosage form. Non-limiting examples of topical dosage forms useful herein include liquids, creams, gels, ointments, foam, solutions, suspensions, lotions, and the like. Non-limiting examples of oral dosage forms useful herein include tables, capsules, liquids, and the like.

Certain solvents including, but not limited to, dimethylsulfoxide (DMSO) capable of dissolving both polar and non-polar compounds is known to easily penetrate the skin of mammals including but not limited to humans and companion animals and to transport small molecules through biological membranes.[62,63] DMSO has also shown efficacy in inflammatory conditions including, but not limited to, rheumatoid arthritis, in modulating the production of pro-inflammatory cytokines/chemokines from human monocytes, the cell in human blood secreting these inflammatory mediators.[23,61]

Certain anti-oxidants including, but not limited to, N-Acetyl Cysteine (NAC), PQQ and Glutathione. NAC, a precursor to glutathione, acts as an excipient free-radical scavenger in stabilizing unsaturated lipids such as DHA. NAC, by modulating the immune response and increasing natural glutathione levels, can further reduce inflammation. Clinical research and practice show NAC is effective, safe, and mostly well tolerated. Therapeutic activity of NAC relies on reduction of oxidative stress, modulation of mitochondrial dysfunction, apoptosis, inflammatory processes, and modulation of glutamate homeostasis.[64]

EXAMPLES

TABLE 1

EXAMPLE NON-CANNABIS INGREDIENT LIST FOR A COMPOSITION TO SUPPLEMENT ENDOCANNABINOID SYSTEM TONE TO BETTER ADDRESS AGE RELATED DISCOMFORT

| INGREDIENT (Liquid or Solid) eCS-TONE ™ | DAILY DOSE RANGE Content Depends on Form | FUNCTION Active Ingredient | FDA STATUS Generally Recognized As Safe |
|---|---|---|---|
| PEA | 100-1200 mg | Anti-Inflammatory | GRAS |
| beta-Caryophyllene | 0.01-0.1 mL/g | Anti-Inflammatory | GRAS |
| Omega 3 DHA | 1.0-10 mg/kg | Anti-Inflammatory-Bioavailability Excipient | GRAS |
| Chlorophyllin | 100-300 mg/day | Anti-Inflammatory Anti-oxidant Bioavailability Excipient | GRAS |
| Humalene | 10-40 mg/kg | Anti-Inflammatory | GRAS |
| Capsaicin | 6-30 mg/day | Anti-Inflammatory (TRPV1) | GRAS |
| dimethylsulphoxide | TBD | Anti-inflammatory-solvent | GRAS |
| Thiamine B1 | 1.2-750 mg/day | Anti-inflammatory | GRAS |
| Pyridoxine B6 | 0.3-50 mg/day | Anti-Noceceptic | GRAS |
| Methylcobalamin B12 | 0.3 mcg-10 mg/day | Analgesic | GRAS |

TABLE 2

Comparison of PEA vs CBD in mitigating inflammation & age-related discomfort

| PEA | CBD |
|---|---|
| Endogenous-naturally made by the mammalian body | Not made in the mammalian body and must be extracted from cannabis |
| Sources: egg yolk, peanuts, lecithin | Sources: cannabis/hemp only |
| Never contains THC | Naturally includes traces of THC |
| No legal considerations hindering use | Legal to grow; taboo in medical settings or some States; Illegal in interstate commerce. |

TABLE 2-continued

Comparison of PEA vs CBD in mitigating inflammation & age-related discomfort

| PEA | CBD |
|---|---|
| Endogenous level decreases with age; data supports benefits of supplementation | Supplementation unnecessary for substance not made in the body |
| Produced in homeostasis as needed in response to pain, stress and tissue damage. | Is not produced in the body at all |
| Activates PPAR-alpha receptor activating numerous key genes in the pain process | Genetic action not established |
| Many randomized clinical trials since 1970s | US clinical trials restrictions due to DEA |
| No deleterious effects noted anywhere in the world since mid 1970's | May have deleterious effects on fetus of pregnant woman (38. Argueta) |
| PEA is neuroprotective; greatly reduces inflammation post trauma and stroke | NA because CBD is less efficacious and not as abundant in the brain as PEA |
| PEA both reduces inflammation as well as aids in tissue healing | Simply down-regulates pain signaling of damaged tissues; no known aid to healing |
| high supplemental PEA inhibit degrading enzymes; extending effective pain reduction | CBD not known to greatly inhibit enzymes that degrade cannabinoids |
| No drug-drug interactions reported; PEA is a pain adjuvant; eventually replacing drugs | Interacts in liver with cytochrome P450 enzymes; not useful as pain relief adjacent |
| Absolutely no side effects | Potential allergic side effects noted |
| PEA is not subject to farming/processing contamination (e.g., heavy metals, bacteria) | CBD is plant derived; not federally regulated; can contain dangerous heavy metals & THC |
| PEA is therapeutic in Parkinson's Disease (PD) trials; PEA is neuroprotective (Esposito) | No reports of CBD in PD clinical trials. CBD not as active in the brain as PEA. |

Any embodiment of the present subject matter may include any of the optional or preferred features of the other embodiments of the present subject matter. The exemplary embodiments herein disclosed are not intended to be exhaustive or to unnecessarily limit the scope of the present subject matter. The exemplary embodiments were chosen and described in order to explain the principles of the present subject matter so that others skilled in the art may practice the present subject matter. Having shown and described exemplary embodiments of the present subject matter, those skilled in the art will realize that many variations and modifications may be made to affect the described subject matter. Many of those variations and modifications will provide the same result and fall within the spirit of the claimed subject matter. It is the intention, therefore, to limit the subject matter only as indicated by the eventual declaration of scope of the claims.

REFERENCES

1. McPartland, J. M. et al. (2014) Care and Feeding of the Endocannabinoid System: a Systematic Review of Potential Clinical Interventions That Up-regulate the Endocannabinoid System. PLoS ONE 9, e89566.)
1a. RUSSO, E. Cannabinoids in the management of difficult to treat pain. Ther Clin Risk Manag. 2008 February; 4(1): 245-259.
2. FDA Public Notice FDA Regulation of *Cannabis* and *Cannabis*-Derived Products, Including Cannabidiol (CBD) https:// www.fda.gov/news-events/public-health-focus/fda-regulation-*Cannabis*-and-*Cannabis*-derived-products-includingcannabidiol-cbd
3. Davis M P, Behm B, Mehta Z, Fernandez C. The Potential Benefits of Palmitoylethanolamide in Palliation: A Qualitative Systematic Review. Am J Hosp Palliat Med. 2019; 36(12):1134-1154.
3a. Keppel Hesselink J M. Evolution in pharmacologic thinking around the natural analgesic palmitoylethanolamide: from nonspecific resistance to PPAR-α agonist and effective nutraceutical. J Pain Research 2013 Aug. 8; 6:625-34.
4. Keppel Hesselink J M. Glia as a new target for neuropathic pain, clinical proof of concept for palmitoylethanolamide, a glia modulator. Anesth Pain Intensive Care 2011; 15: 143-5.
5. O'Sullivan, S. E. (2007). "Cannabinoids go nuclear: evidence for activation of peroxisome proliferator-activated receptors". British Journal of Pharmacology. 152 (5): 576-582.
6. Keppel Hesselink, J M (2012). "New Targets in Pain, Non-Neuronal Cells, and the Role of Palmitoylethanolamide" (review). The Open Pain Journal. 5: 12-23.
7. Keppel Hesselink J M, de Boer T, Witkamp R F (2013). "Palmitoylethanolamide: A Natural Body-Own Anti-Inflammatory Agent, Effective and Safe against Influenza and Common Cold". International Journal of Inflammation. 2013: 1-8.
8. Lo Verme, J.; Fu, J.; Astarita, G.; La Rana, G.; Russo, R.; Calignano, A.; Piomelli, D. (2005). "The nuclear receptor peroxisome proliferator-activated receptor-alpha mediates the anti-inflammatory actions of palmitoylethanolamide". Molecular Pharmacology. 67 (1): 15-19.
9. Godlewski, G.; Offertáler, L.; Wagner, J. A.; Kunos, G. (2009). "Receptors for acylethanolamides-GPR55 and GPR119". Prostaglandins & Other Lipid Mediators. 89 (3-4): 105-297.
10. O'Sullivan, S. E.; Kendall, D. A. (2010). "Cannabinoid activation of peroxisome proliferator-activated receptors: Potential for modulation of inflammatory disease". Immunobiology. 215 (8): 611-616.
11. Jonsson, K. O.; Vandevoorde, S. V.; Lambert, D. M.; Tiger, G.; Fowler, C. J. (2001). "Effects of homologues and analogues of palmitoylethanolamide upon the inactivation of the endocannabinoid anandamide". British Journal of Pharmacology. 133 (8): 1263-1275.
12. Ho, W. S.; Barrett, D. A.; Randall, M. D. (2008). "'Entourage' effects of N-palmitoylethanolamide and N-oleoylethanolamide on vasorelaxation to anandamide occur through TRPV1 receptors". British Journal of Pharmacology. 155 (6): 837-846.
13. De Filippis, D.; d'Amico, A.; Cipriano, M.; Petrosino, S.; Orlando, P.; Di Marzo, V.; Iuvone, T. (2010). "Levels of endocannabinoids and palmitoylethanolamide and their pharmacological manipulation in chronic granulomatous inflammation in rats". Pharmacological Research. 61 (4): 321-328.
14. Atakan Z. *Cannabis*, a complex plant: different compounds and different effects on individuals. Therapeutic Advances in Psychopharmacology. December 2012:241-254.
15. Calignano a, L. R. G. (2001). "Antinociceptive activity of the endogenous fatty acid amide, palmitoylethanolamide". Eur J Pharmacol. 419 (2-3): 191-198.
16. Koch, M.; Kreutz, S.; Bottger, C.; Benz, A.; Maronde, E.; Ghadban, C.; Korf, H. W.; Dehghani, F. (2010). "Palmitoylethanolamide Protects Dentate Gyrus Granule Cells via Peroxisome Proliferator-Activated Receptor-Alpha". Neurotoxicity Research. 19 (2): 330-340.
17. Lambert D M, Vandevoorde S, Diependaele G, Govaerts S J, Robert A R (2001). "Anticonvulsant activity of Npalmitoylethanolamide, a putative endocannabinoid, in mice". Epilepsia. 42 (3): 321-7.
18. G.R.A.S. Federal Register Notice—the GRAS Final Rule (81 FR 54960—Aug. 17, 2016) https://www.federalregister.gov/documents/2016/08/17/2016-19164/substances-generally-recognized-as-safe
19. Alhouayek M. et al, Controlling 2-arachidonoylglycerol metabolism as an anti-inflammatory strategy. Drug Discovery Today Volume 19, Number 3 2014 p 295-304.
20. Russo, E. et al. (2002) in Search of Plants, Other Than *Cannabis sativa*, With Cannabinoid Receptor Activity. In Symposium on the Cannabinoids. International Cannabinoid Research Society, pp. 46.
21. Epidiolex approved by FDA https://www.accessdata.fda.gov/drugsatfda_docs/nda/2018/210365Orig1s000TOC.cfm
22. Merskey H, Bogduk N. Classification of chronic pain. 2nd ed. Seattle: IASP Press, 1994. p. 1.
23. Bonica J J. The management of pain. Philadelphia: Lea & Febiger, 1953.
24. Breivik H, Collett B, Ventafridda V, Cohen R, Gallacher D. Survey of chronic pain in Europe: prevalence, impact on daily life, and treatment. Eur J Pain 2006; 10:287.
25. Goldberg D S, Summer J M. Pain as a global public health priority. BMC Public Health 2011; 11:770.
26. Institute of Medicine (IOM). Relieving pain in America: a blueprint for transforming prevention, care, education, and research. Washington, D C: The National Academies Press, 2011.
27. Julius D. TRP Channels and Pain The Annual Review of Cell and Developmental Biology. 2013. 29:355-84
27a. Russo, Ethan B (2011). "Taming THC: Potential *Cannabis* Synergy and Phytocannabinoid-Terpenoid Entourage Effects". British Journal of Pharmacology. 163 (7): 1344-1364.
28. Shenglong Zou and Ujendra Kumar. Cannabinoid Receptors and the Endocannabinoid System: Signaling and Function in the Central Nervous System. Int. J. Mol. Sci. 2018, 19(3), 833.
28a. Ben-Shabat, Shimon; Fride, Ester; Sheskin, Tzviel; Tamiri, Tsippy; Rhee, Man-Hee; Vogel, Zvi; Bisogno, Tiziana; De Petrocellis, Luciano; Di Marzo, Vincenzo; Mechoulam, Raphael (July 1998). "An Entourage Effect: Inactive Endogenous Fatty Acid Glycerol Esters Enhance 2-Arachidonoyl-Glycerol Cannabinoid Activity". European Journal of Pharmacology. 353 (1): 23-31.
29. E. B. Russo, "Cannabinoids in the management of difficult to treat pain." Therapeutics and Clinical Risk Management, vol. 4, no. 1, pp. 245-259, 2008
30. M. Zhang, B. R. Martin, M. W. Adler, R. K. Razdan, J. I. Jallo, and R. F. Tuma, "Cannabinoid CB2 receptor activation decreases cerebral infarction in a mouse focal ischemia/reperfusion model," Journal of Cerebral Blood Flow and Metabolism, vol. 27, no. 7, pp. 1387-1396, 2007.
31. Fiorenzani, P., S. Lamponi, A. Magnani, I. Ceccarelli, and A. M. Aloisi. 2014. In Vitro and In Vivo characterization of the new analgesic combination Beta-caryophyllene and docosahexaenoic acid. Evid. Based Complement. Alternat. Med. 2014
31a. Gertsch, J., Leonti, M., et al. (2008) Beta-caryophyllene is a dietary cannabinoid. Proceedings of the National Academy of Sciences: 105, 26, 9099-9104
32. Piscitelli F, Di Marzo V. "Redundancy" of endocannabinoid inactivation: new challenges and opportunities for pain control. ACS Chem Neurosci. 2012; 3(5):356-363.]
33. Medeiros, R., G. F. Passos, C. E. Vitor, J. Koepp, T. L. Mazzuco, L. F. Pianowski, et al. 2007. Effect of Two Active Compounds Obtained From the Essential Oil of Cordia Verbenacea on the Acute Inflammatory Responses Elicited by LPS in the Rat Paw. Br. J. Pharmacol. 151: 618-627.
33a. Silver R J. The Endocannabinoid System of Animals. Animals (Basel). 2019 Sep. 16; 9(9):686
34. A. L. Klauke, I. Racz, B. Pradier, et al. The cannabinoid CB2 receptor-selective phytocannabinoid beta-caryophyllene exerts analgesic effects in mouse models of inflammatory and neuropathic pain Eur Neuropsychopharmacol, 24 (4) (2014), pp. 608-620
34a. Mallinson, Tom (2017). "A review of ketorolac as a prehospital analgesic". Journal of Paramedic Practice. London: M A Healthcare. 9 (12): 522-526.
35. Ray W A, Disease C H, Varas-Lorenzo C, Chung C P, Castellsague J, Murray K T, et al. Cardiovascular risks of nonsteroidal antiinflammatory drugs in patients after hospitalization for serious. Circ Cardiovasc Qual Outcomes. 2009
36. Pacher, P. and Kunos, G. (2013) Modulating the Endocannabinoid System in Human Health and Disease—Successes and Failures. FEBS J. 280, 1918-1943)
37. Russo, E. B. (2004) Clinical Endocannabinoid Deficiency (CECD): Can This Concept Explain Therapeutic Benefits of *Cannabis* in Migraine, Fibromyalgia, Irritable Bowel Syndrome and Other Treatment-Resistant Conditions? Neuroendocrinol. Lett. 25, 31-39
37a. U.S. Pat. No. 6,630,507 Cannabinoids as Antioxidants and Neuroprotectants.
38. Argueta D A, Ventura C M, et al. A Balanced Approach for Cannabidiol Use in Chronic Pain. Front Pharmacol. 2020; 11: 561
39. Cravatt B F, Giang D K, Mayfield S P, Boger D L, Lerner R A, Gilula N B. Molecular characterization of an enzyme that degrades neuromodulatory fatty-acid amides. Nature. 1996; 384:83-87.
39a. Endocannabinoid System . . . What Is It? (https://www.crescolabs.com/endocannabinoid-system/)
40. What Is Homeostasis? https://www.scientificamerican.com/article/what-is-homeostasis/.)
40a. Yatoo M I et al., Anti-Inflammatory Drugs and Herbs with Special Emphasis on Herbal Medicines for Countering Inflammatory Diseases and Disorders—A Review. Recent Patents on Inflammation & Allergy Drug Discovery. 12 (1)
41. Chovatiya R and Medzhitov R. (2014) Stress, Inflammation, and Defense of Homeostasis. Molecular Cell 54

41a. A Conversation With Dr. Ethan Russo On CBD & Clinical Endocannabinoid Deficiency https://www.projectcbd.org/science/cbd-clinical-endocannabinoid-deficiency-dr-ethan-russo)
42. Chapkin, R. S., W. Kim, J. R. Lupton, and D. N. McMurray. 2009. Dietary docosahexaenoic and eicosapentaenoic acid: emerging mediators of inflammation. Prostaglandins Leukot. Essent. Fatty Acids 81:187-191.
43. Stillwell W, Wassail S R. Docosahexaenoic acid: membrane properties of a unique fatty acid. Chem Phys Lipids. 2003; 126:1-27.
44. Baigent C, Bhala N, Emberson J, Merhi A, Abramson S, Arber N, et al. Vascular and upper gastrointestinal effects of non-steroidal anti-inflammatory drugs: Meta-analyses of individual participant data from randomized trials. Lancet. 2013; 382(9894):769-79.
45. Keppel Hesselink J M. Evolution in pharmacologic thinking around the natural analgesic palmitoylethanolamide: from nonspecific resistance to PPAR-α agonist and effective nutraceutical. J Pain Res. 2013 Aug. 8; 6:625-34.
46. Keppel Hesselink J M. 2018. Chronic Pain and the Use Of PalmetoyleEthanolAmide. Journal of the Neurological Sciences. 5(2):104248.
47. Ferrero-Miliani L, Nielsen O H, Andersen P S, Girardin S E; Nielsen; Andersen; Girardin (February 2007). "Chronic inflammation: importance of NOD2 and NALP3 in interleukin-1beta generation". Clin. Exp. Immunol. 147 (2): 227-35.
48. Federal Trade Commission Announcement. FTC Announces Crackdown on Deceptively Marketed CBD Products. Dec. 17, 2020 (https://www.ftc.gov/news-events/press-releases/2020/12/ftc-announces-crackdown-deceptively-marketed-cbdproducts)
49. Skaper S D, Facci L, and Giusti P. Glia and mast cells as targets for palmitoylethanolamide, an anti-inflammatory and neuroprotective lipid mediator. Mol Neurobiol. 2013 October; 48(2):340-52
50. Placement in Schedule V of Certain FDA-Approved Drugs Containing Cannabidiol: Final Order. U S Drug Enforcement Administration, Department of Justice. Fed Regist. 2018 Sep. 28; 83(189):48950-3.
51. Astarita, G., Geaga, J., Ahmed, F., and Piomelli, D. (2009) Targeted lipidomics as a tool to investigate endocannabinoid function. Int. Rev. Neurobiol. 85,35-55.
52. Reddy, A S, and Zhang, S. (2013) Polypharmacology: drug discovery for the future. Expert Rev. Clin. Pharmacol. 6, 41-47.
53. De Filippis, D.; d'Amico, A.; Cipriano, M.; Petrosino, S.; Orlando, P.; Di Marzo, V.; Iuvone, T.; Iuvone, T. (2010). "Levels of endocannabinoids and palmitoylethanolamide and their pharmacological manipulation in chronic granulomatous inflammation in rats". Pharmacological Research. 61 (4): 321-328.
54. Philip C. Calder Omega-3 Fatty Acids and Inflammatory Processes. Nutrients. 2010 March; 2(3): 355-374.
55. Ulbricht, C E, et al. (2014). An Evidence-Based Systematic Review of Chlorophyll by the Natural Standard Research Collaboration. Journal of Dietary Supplements, 2014
56. Varga, et al, (2017) Beta-Caryophyllene Protects Against Alcoholic Steatohepatitis by Attenuating Inflammation and Metabolic Dysregulation in Mice. British Journal of Pharmacology (2018) 175 320-334
57. Jolayemi and Ojewole (2913) Comparative Anti-Inflammatory Properties of Capsaicin and Ethyl-Acetate Extract of *Capsicum frutescens* in Rats. Afr Health Sci. 2013 June; 13(2): 357-361.
58. Wei & Manickam (2012) Response Surface Methodology, an Effective Strategy in the Optimization of the Generation of Curcumin-Loaded Micelles. Asia-Pacific Journal of Chemical Engineering Volume 7, Issue 51
59. Yousef S A, et al. (2019) Mechanistic Evaluation of Enhanced Curcumin Delivery through Human Skin In Vitro from Optimized Nano-emulsion Formulations Fabricated with Different Penetration Enhancers, Pharmaceutics 2019, 11(12), 639
60. FDA's SCOGS Database; Silicon Dioxides, Report No. 61, 1979.; ID Code: 14808-60-7; http://www.acces sdatalda.gov/scripts/fcn/fcnDetailNavigation.cfm?rpt=scogsListing&id=276; accessed Aug. 12, 2011)]
61. Kathrin-Maria Roy "Sulfones and Sulfoxides" in Ullmann's Encyclopedia of Industrial Chemistry, 2002, Wiley-VCH, Weinheim. doi:10.1002/14356007.a25_487
62. Trice J M, Pinals R S. DimethylSulfoxide: a Review of its Use in the Rheumatic Disorders. Seminars in Arthritis and Rheumatism. 1985; 15: 45-60.
63. Muir M. DMSO. Alternative and Complementary Therapies. 1996; 2: 230-235. 10.1089/act.1996.2.230
64. Uraz S, et. al., N-acetylcysteine expresses powerful anti-inflammatory and antioxidant activities resulting in complete improvement of acetic acid-induced colitis in rats. Scandinavian Journal of Clinical and Laboratory Investigation. 2013 February; 73(1):61-6.
65. Vetter G, Bruggemann G, Lettko M, et al. Shortening diclofenac therapy by B vitamins. Results of a randomized double-blind study, diclofenac 50 mg versus diclofenac 50 mg plus B vitamins, in painful spinal diseases with degenerative changes. Z Rheumatol 1988; 47(5):351-62.
66. Ponce-Monter H A, Ortiz M I, Garza-Hernandez A F, Monroy-Maya R, Soto-Rios, M, Carrillo-Alarcon L, et al. Effect of diclofenac with B vitamins on the treatment of acute pain originated by lower-limb fracture and surgery. Pain Res Treat. 2012; 2012:104782.
67. Munvar Miya Shaik, Siew Hua Gan, "Vitamin Supplementation as Possible Prophylactic Treatment against Migraine with Aura and Menstrual Migraine", BioMed Research International, vol. 2015, Article ID 469529, 10 pages, 2015.
68. Otten J J, Pitzi Hellwing J, Meyers L D (2009) Dietary Reference Intakes: Essential Guide to Nutrient Requirements. National Academies Press, Washington, D.C.
69. Shideler C. Vitamin B6: an overview. Am J Med Technol. 1983; 49(1):17-22.
70. Calderon-Ospina C A, Nava-Mesa M O. B Vitamins in the nervous system: Current knowledge of the biochemical modes of action and synergies of thiamine, pyridoxine, and cobalamin. CNS Neurosci Ther. 2020 January; 26(1):5-13.
71. Geller, Mauro & Oliveira, Lisa & Nigri, Rafael & Mezitis, Spyros & Ribeiro, Marcia & Fonseca, Adenilson & Guimaraes, Oscar & Kaufman, Renato & Wajnsztajn, Fernanda. (2017). B Vitamins for Neuropathy and Neuropathic Pain. Vitamins & Minerals. 06. 10.4172/2376-1318.1000161.
72. Garg S, Syngle A, Vohra K. Efficacy and tolerability of advanced glycation end-products inhibitor in osteoarthritis: a randomized, double-blind, placebo-controlled study. Clin J Pain. 2013; 29(8):717-24.

73. Mibielli M A, Geller M, Cohen J C, Goldberg S G, Cohen M T, Nunes C P, et al. Diclofenac plus B vitamins versus diclofenac monotherapy in lumbago: the DOLOR study. Curr Med Res Opin. 2009; 25(11):2589-99.

What is claimed:

1. A method of treating inflammatory and neuropathic pain in a mammal comprising:
   administering to a mammal in need thereof a synergistic pharmaceutical daily dosage form comprising: between about 1 and about 2% by weight of palmitoylethanolamide (PEA) in an ultramicronized form, between about 10 and about 30% by weight of beta-caryophyllene (BCP) and between about 10 and about 30% by weight of docosahexaenoic acid (DHA) in liquid form;
   wherein a daily dose of the palmitoylethanolamide (PEA) does not exceed about 1200 mg/day, a daily dose of the beta-caryophyllene (BCP) does not exceed about 0.1 mL/kg per kg body weight of the mammal, and a daily dose of the docosahexaenoic acid (DHA) does not exceed about 10 mg/kg per kg body weight of the mammal.

2. The method of claim 1, wherein the pharmaceutical daily dosage form is an oral or topical dosage form.

3. The method of claim 1, wherein the pharmaceutical daily dosage form further comprises one or more compounds with anti-inflammatory activity in a total weight percentage ranging between 0 and about 20%.

4. The method of claim 3, wherein the one or more compounds with anti-inflammatory activity is selected from the group consisting of plant derived terpenes/terpenoids, polyphenols, B vitamins, and combinations thereof.

5. The method of claim 4, wherein the one or more compounds with anti-inflammatory activity, comprises a terpene comprising one or more of beta-carophyllene and humalene.

6. The method of claim 3, wherein the one or more compounds with anti-inflammatory activity is one or more polyphenols.

7. The method of claim 6, wherein the one or more compounds with anti-inflammatory activity comprises a polyphenol selected from the group consisting of Flavonoids, Polyphenolic amides, curcumin, and combinations thereof.

8. The method of claim 7, wherein the one or more compounds with anti-inflammatory activity are quercetin, a capsaicinoid, and curcumin.

9. The method of claim 3, wherein the synergistic pharmaceutical daily dosage form is in the form of a tablet, a capsule, or liquid.

10. The method of claim 3, wherein the one or more compounds with the anti-inflammatory activity is comicronized with the palmitoylethanolamide.

11. The method of claim 1, wherein the neuropathic pain results from a disease selected from the group consisting of both acute and chronic painful central and peripheral neuropathies; migraines; fibromyalgia; pain associated with vertebral column and spinal cord diseases of traumatic, dysmetabolic and degenerative origin; acute and/or chronic pain associated with diseases in the pelvic area; Irritable Bowel Syndrome; pain associated with traumatic and degenerative joint diseases; pain associated with arthritic diseases, and any combination thereof.

12. The method of claim 1, wherein the palmitoylethanolamide is in ultra-micronized form (um PEA) with a particle size ranging between about 0.8 and about 6 microns.

13. A method of treating neuropathic and inflammatory pain in a mammal, comprising: administering to a mammal in need thereof a dosage form selected from the group consisting of a chew, tablet, capsule, or a liquid form of a synergistic pharmaceutical composition, wherein each dosage form of the pharmaceutical composition comprises: palmitoylethanolamide (PEA) in a weight percentage between about 1 and about 2%, beta-caryophyllene (BCP) in a weight percentage between about 10 and about 30% and docosahexaenoic acid (DHA) in a weight percentage between about 10 and about 30% and one or more compounds with anti-inflammatory activity in a total weight percentage ranging between 0 and about 20%.

14. The method of claim 13, wherein said palmitoylethanolamide is in non-micronized form with a particle size ranging between about 50 and about 100 µm, in micronized form (mPEA) with a particle size ranging between about 2 and about 10 µm, or in ultra-micronized form (umPEA) with a particle size ranging between about 0.8 and about 6 µm, or in a mixture of such forms.

15. The method of claim 13, wherein said beta-caryophyllene (BCP) and docosahexaenoic acid is in a miscible form.

16. The method of claim 2, wherein the pharmaceutical daily dosage form is topical dosage form.

17. The method of claim 16, wherein the topical dosage form is selected from the group consisting of a transdermal patch, a cream, a lotion, an ointment, and a powder.

18. The method of claim 1, wherein the pharmaceutical daily dosage form further comprises one or more of cannabigerol (CBG), cannabidiol (CBD) and cannabidiolic acid (CBDA).

* * * * *